United States Patent
Marchesini et al.

(10) Patent No.: US 12,178,228 B2
(45) Date of Patent: Dec. 31, 2024

(54) POWDERED THICKENER MAINTAINING ITS EXTENSIONAL PROPERTIES WHEN RECONSTITUTED AND FOR PROMOTING SAFE SWALLOWING BY INDIVIDUALS WITH DYSPHAGIA

(71) Applicant: SOCIETE DES PRODUITS NESTLE S.A., Vevey (CH)

(72) Inventors: Giulia Marchesini, Bern (CH); Jan Engmann, Lausanne (CH); Christoph Widmer, Kehrsatz (CH); Thibaut Dutter, Bern (CH)

(73) Assignee: Societe des Produits Nestle S.A., Vevey (CH)

( * ) Notice: Subject to any disclaimer, the term of this patent is extended or adjusted under 35 U.S.C. 154(b) by 695 days.

(21) Appl. No.: 16/620,083

(22) PCT Filed: Jun. 7, 2018

(86) PCT No.: PCT/EP2018/065002
§ 371 (c)(1),
(2) Date: Dec. 6, 2019

(87) PCT Pub. No.: WO2018/224590
PCT Pub. Date: Dec. 13, 2018

(65) Prior Publication Data
US 2020/0187540 A1   Jun. 18, 2020

Related U.S. Application Data

(60) Provisional application No. 62/516,444, filed on Jun. 7, 2017.

(51) Int. Cl.
*A23L 29/269* (2016.01)
*A23L 2/39* (2006.01)
(Continued)

(52) U.S. Cl.
CPC ............ *A23L 29/271* (2016.08); *A23L 2/39* (2013.01); *A23L 29/212* (2016.08); *A61K 9/0095* (2013.01); *A61K 9/145* (2013.01)

(58) Field of Classification Search
None
See application file for complete search history.

(56) References Cited

U.S. PATENT DOCUMENTS

2004/0258829 A1   12/2004   Zheng et al.
2006/0204634 A1   9/2006   Wuersch et al.
(Continued)

FOREIGN PATENT DOCUMENTS

CN   101102681 A   1/2008
CN   103354719 A   10/2013
(Continued)

OTHER PUBLICATIONS

Burbidge: EP 3010355 A1, published May 27, 2016, filed May 16, 2014. (Year: 2014).*

(Continued)

*Primary Examiner* — Patricia A George
(74) *Attorney, Agent, or Firm* — K&L Gates LLP

(57) ABSTRACT

A thickening powder promotes safe swallowing of a composition by an individual with dysphagia and can be used in methods of treating dysphagia, promoting safe swallowing of a composition, and mitigating a risk of aspiration during swallowing of a composition. The powder contains beta-glucan and maltodextrin in an amount that is neutral toward or enhances the extensional properties of the composition. Optionally the thickening powder can also include a low molecular weight carbohydrate such as sucrose or lactose. The powder can be diluted in a liquid comprising at least one (Continued)

of water or milk to form at least a portion of a composition such as a nutritional product and to improve the cohesiveness of the composition.

4 Claims, 3 Drawing Sheets

(51) Int. Cl.
*A23L 29/212* (2016.01)
*A61K 9/00* (2006.01)
*A61K 9/14* (2006.01)

(56) References Cited

U.S. PATENT DOCUMENTS

2013/0045297 A1* 2/2013 Knight ................. A23L 33/105
426/2
2015/0208706 A1 7/2015 Patel et al.

FOREIGN PATENT DOCUMENTS

| CN | 105473003 A | 4/2016 |
| EP | 2842432 | 3/2015 |
| JP | 2016049022 A | 4/2016 |
| WO | 2016012403 | 1/2016 |

OTHER PUBLICATIONS

Takeiti: Morphological and Physicochemical Characterization of Commercial Maltodextrins With Different Degrees of Dextrose-Equivalent; International Journal of Food Properties, 13: 411-425, 2010. (Year: 2010).*
Anttila et al. "Viscosity of beta-glucan in oat products" Agricultural and Food Science, 2004, vol. 13, pp. 80-87.
Mintel "Curl & Bounce Tonic" Apr. 2016, pp. 1-6, XP055498008, retrieved from the Internet: URL:http://www.gnpd.com/sinatra/recordpage/3882497/from_search/8s6eVyaEXA/?page=4.
Chronakis et al., "Solid-state Characteristics and Redispersible Properties of Powders Formed by Spray-Drying and Freeze-Drying Cereal Dispersions of Varying (1→3,1→4)-β-glucan Content", Journal of Cereal Science, vol. 40, 2004, pp. 183-193.
Brazil Office Action for Appl No. BR112019023341-5 dated Jun. 27, 2023.
Lazaridou et al., "A Comparative Study on Structure-Function Relations of Mixed-Linkage (1→3), (1→4) Linear β-D-Glucans", Food Hydrocolloids, vol. 18, Issue No. 5, 2004, pp. 837-855.
China Patent Office Communication for Application No. 201880029444.4, dated Feb. 9, 2022, 30 pages.
"Calbee", Amazon, Dec. 9, 2016, pp. 1-8.
"Calbee", Amazon, Mar. 12, 2017, pp. 1-6.
Japan Patent Office Action for Application No. 2019-562385, Dispatch No. 196264, Dispatch Date April 26, 2022, 12 pages.

* cited by examiner

| Addition point | Sample | pH | η (50/s) avg mPa.s | Break up time avg | stdev |
|---|---|---|---|---|---|
| | Reference | 7.12 | 25.25 | 0.283 | 0.019 |
| After extraction | Promitor | 6.92 | 12.25 | *0.004* | |
| After extraction | Maltodextrin | 6.91 | 13.86 | 0.027 | 0.030 |
| | Reference | 6.00 | 24.88 | 0.284 | 0.014 |
| After extraction | Promitor | 6.00 | 12.30 | *0.003* | |
| After extraction | Maltodextrin | 6.00 | 14.34 | 0.051 | 0.008 |
| Before extraction | Maltodextrin | 6.87 | 59.97 | 0.420 | 0.039 |
| Before extraction | Promitor | n.m. | 12.37 | 0.000 | |
| Before extraction | Maltodextrin | 6.00 | 59.18 | 0.403 | 0.041 |

FIG. 2

POWDERED THICKENER MAINTAINING ITS EXTENSIONAL PROPERTIES WHEN RECONSTITUTED AND FOR PROMOTING SAFE SWALLOWING BY INDIVIDUALS WITH DYSPHAGIA

CROSS REFERENCE TO RELATED APPLICATIONS

The present application is a National Stage of International Application No. PCT/EP2018/065002, filed on Jun. 7, 2018, which claims priority to U.S. Provisional Patent Application No. 62/516,444, filed on Jun. 7, 2017, the entire contents of which are being incorporated herein by reference.

BACKGROUND

The present disclosure generally relates to a powdered thickener for promoting safe swallowing of a composition by an individual with dysphagia, a method of treating dysphagia by administering a composition made by dilution of a powdered thickener, a method of making a powdered thickener, and a method of improving the cohesiveness of a composition by diluting a powdered thickener. The powdered thickener maintains its extensional properties when reconstituted.

Dysphagia is a medical term for the symptom of difficulty in swallowing. Dysphagia may be a sensation that suggests a difficulty in a passage of a solid or a liquid (i.e., a nutritional product) from the mouth to the stomach.

During processing of a nutritional product in the mouth and during swallowing, a viscosity of the nutritional product changes due to shear forces. In most cases, the viscosity of the nutritional product decreases when the shear forces and the shear rate acting on the nutritional product (e.g., chewing forces) increase. Individuals who suffer from dysphagia often require a thickened nutritional product. Thickening of the nutritional product is achieved to increase, in particular, the shear viscosity of the product by adding a thickener such as a starch or gum thickener. The thickened nutritional product makes an individual with dysphagia less likely to aspirate during passage of the nutritional products from the mouth to the stomach.

Individuals with dysphagia may find that nutritional products cause coughing, spluttering or even choking, and therefore thickened nutritional products enable the individuals who suffer from dysphagia to swallow safely. The addition of a thickener is thought to improve a bolus control and timing of swallowing, but the resultant thickness is disliked by individuals who suffer from dysphagia due to the extra swallowing effort required. Moreover, the thickener leaves residues with high levels of viscosity, resulting in undesirable organoleptic properties. This is particularly relevant for liquids and beverages, as a dysphagia patient would expect a liquid that still has the organoleptic properties of a real thin liquid instead of a liquid product showing high viscosity. Furthermore, thickened nutritional products wherein merely shear viscosity is increased usually lack the cohesiveness that saliva typically provides to food boluses.

Dysphagia is classified into three major types: oropharyngeal dysphagia, esophageal dysphagia and functional dysphagia.

Oropharyngeal dysphagia is generally not treatable with medication. Oropharyngeal dysphagia affects individuals of all ages but is more prevalent in older individuals. Worldwide, oropharyngeal dysphagia affects approximately 22 million people over the age of 50 years. Oropharyngeal dysphagia is often a consequence of an acute event such as a stroke, brain injury, or surgery for oral or throat cancer. In addition, radiotherapy and chemotherapy may weaken the muscles and degrade the nerves associated with the physiology and nervous innervation of the swallow reflex. Oropharyngeal dysphagia is also common for individuals with progressive neuromuscular diseases, such as Parkinson's disease, to experience increasing difficulty in swallowing initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, Tardive dyskinesia, metabolic encephalopathies, amyotrophic lateral sclerosis, Parkinson's disease, dementia), infectious illnesses (diphtheria, botulism, Lyme disease, syphilis, mucositis [herpetic, cytomegalovirus, candida, etc.]), autoimmune illnesses (lupus, scleroderma, Sjogren's syndrome), metabolic illnesses (amyloidosis, Cushing's syndrome, thyrotoxicosis, Wilson's disease), myopathic illnesses (connective tissue 15 disease, dermatomyositis, myasthenia gravis, myotonic dystrophy, oculopharyngeal dystrophy, polymyositis, sarcoidosis, paraneoplastic syndromes, inflammatory myopathy), iatrogenic illnesses (medication side effects [e.g., chemotherapy, neuroleptics, etc.], post surgical muscular or neurogenic, radiation therapy, corrosive [pill injury, intentional]), and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Esophageal dysphagia can affect individuals of all ages. Esophageal dysphagia is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g., peptic stricture secondary to gastroesophageal reflux disease, esophageal rings and webs [e.g., sideropenic dysphagia or Plummer-Vinson syndrome], esophageal tumors, chemical injury [e.g., caustic ingestion, pill esophagitis, sclerotherapy for varices], radiation injury, infectious esophagitis, and eosinophilic esophagitis). Mediastinal (extrinsic) diseases obstruct the esophagus by direct invasion or through lymph node enlargement associated with various conditions (tumors [e.g., lung cancer, lymphoma], infections [e.g., tuberculosis, histoplasmosis], and cardiovascular [dilated auricula and vascular compression]). Neuromuscular diseases may affect the esophageal smooth muscle and its innervation, disrupting peristalsis or lower esophageal sphincter relaxation, or both, commonly associated with various conditions (achalasia [both idiopathic and associated with Chagas disease], scleroderma, other motility disorders, and a consequence of surgery [i.e., after fundoplication and antireflux interventions]). Individuals with intraluminal foreign bodies commonly experience acute esophageal dysphagia.

Functional dysphagia is defined in some patients wherein no organic cause for dysphagia can be found.

Dysphagia is not generally diagnosed. Dysphagia has major consequences on health and healthcare costs on individuals who suffer from dysphagia. Individuals who suffer from severe dysphagia experience a sensation of impaired passage of nutritional products from the mouth to the stomach, occurring immediately after swallowing. Among community dwelling individuals, perceived symptoms may bring the individuals who suffer from dysphagia to see a doctor. Among institutionalized individuals, health care practitioners may observe symptoms or hear comments from the individual who suffers from dysphagia or a family member suggestive of swallowing impairment and then recommend evaluation of the individual who suffers from dysphagia by a specialist. The general awareness of swallowing impairments is low among front-line practitioners, so dysphagia often is undiagnosed and untreated. Yet, a patient can be clinically evaluated and dysphagia diagnosis can be determined through referral to a swallowing specialist (e.g. speech language pathologist).

The general awareness of swallowing impairments is low among front-line practitioners. Many people (especially those who are elderly) suffer with undiagnosed and untreated swallowing impairments. One reason is that front-line community care practitioners (e.g., general practitioners/geriatricians, home care nurses, physical therapists, etc.) do not typically screen for the condition. If they are aware of the severity of swallowing impairments, they commonly do not use an evidence-based method of screening.

A severity of dysphagia may vary from: (i) minimal (perceived) difficulty in safely swallowing nutritional products, (ii) an inability to swallow nutritional products without significant risk for aspiration or choking, and (iii) a complete inability to swallow nutritional products. An inability to properly swallow nutritional products may be due to food boluses of the nutritional products being broken into smaller fragments, which may enter the airway or leave unwanted residues in the oropharyngeal and/or esophageal tract during the swallowing process (e.g., aspiration). If enough material enters the lungs, the patient may drown on the nutritional products that have accumulated in the lungs. Even small volumes of aspirated nutritional products may lead to bronchopneumonia infection, and chronic aspiration may lead to bronchiectasis and may cause some cases of asthma.

Silent aspiration is a common condition among the elderly and refers to the aspiration of the oropharyngeal contents during sleep. People may compensate for less-severe swallowing impairments by self-limiting the diet. The aging process itself, coupled with chronic diseases such as hypertension or osteoarthritis, predisposes the elderly to subclinical dysphagia that may go undiagnosed and untreated until a clinical complication such as pneumonia, dehydration, malnutrition and related complications occurs.

Dysphagia and aspiration impacts upon quality of life, morbidity and mortality. Twelve-month mortality is high (45%) among individuals in institutional care who have dysphagia and aspiration. The economic burden of the clinical consequences arising from lack of diagnosis and early management of dysphagia are therefore significant.

As noted, pneumonia is a common clinical consequence of dysphagia. Pneumonia may require acute hospitalization and emergency room visits. Among those that develop pneumonia due to aspiration, the differential diagnosis of 'aspiration pneumonia' is not necessarily indicated as a result of current care practices.

Pneumonia is life threatening among persons with dysphagia, and the odds of death within 3 months are about 50% (van der Steen et al. 2002). In addition, an acute insult such as pneumonia often initiates the downward spiral in health among elderly. An insult is associated with poor intakes and inactivity, resulting in malnutrition, functional decline, and frailty. Specific interventions (e.g., to promote oral health, help restore normal swallow, or reinforce a swallow-safe bolus) would benefit persons at risk for (due to aspiration of oropharyngeal contents, including silent aspiration) or experiencing recurrent pneumonia.

Similar to pneumonia, dehydration is a life-threatening clinical complication of dysphagia. Dehydration is a common co-morbidity among hospitalized individuals with neurodegenerative diseases (thus, likely to have a swallowing impairment). Nevertheless, dehydration is an avoidable clinical complication of dysphagia. This underlines the need for thin liquids that can be safely consumed and are organoleptically acceptable for people with dysphagia.

Malnutrition and related complications (e.g., [urinary tract] infections, pressure ulcers, increased severity of dysphagia [need for more-restricted food options, tube feeding, and/or Percutaneous Endoscopic Gastrostomy (PEG) tube placement and reduced quality of life], dehydration, functional decline and related consequences [falls, dementia, frailty, loss of mobility, and loss of autonomy]) can arise when swallowing impairment leads to fear of choking on food and liquids, slowed rate of consumption, and self-limited food choices. If uncorrected, inadequate nutritional intake exacerbates dysphagia as the muscles that help facilitate normal swallow weaken as physiological reserves are depleted. Malnutrition is associated with having more than 3-times greater risk of infection. Infections are common in individuals with neurodegenerative diseases (thus, likely to have a chronic swallowing impairment that jeopardizes dietary adequacy).

Malnutrition has serious implications for patient recovery. Malnourished patients have longer length of hospital stay, are more likely to be re-hospitalized, and have higher costs for hospital care. Furthermore, malnutrition leads to unintentional weight loss and predominant loss of muscle and strength, ultimately impairing mobility and the ability to care for oneself. With the loss of functionality, caregiver burden becomes generally more severe, necessitating informal caregivers, then formal caregivers, and then institutionalization. However, malnutrition is an avoidable clinical complication of dysphagia.

Among persons with neurodegenerative conditions (e.g., Alzheimer's disease), unintentional weight loss (a marker of malnutrition) precedes cognitive decline. In addition, physical activity can help stabilize cognitive health. Thus, nutritional adequacy is important among persons with neurodegenerative conditions to help them have the strength and endurance to participate in regular therapeutic exercise and guard against unintentional weight loss, muscle wasting, loss of physical and cognitive functionality, frailty, dementia, and progressive increase in caregiver burden.

Falls and related injuries are a special concern among elderly with neurodegenerative conditions, associated with loss of functionality. Falls are the leading cause of injury deaths among older adults. Falls are reasonably preventable reason by applying evidence-based practices including medical nutrition therapy as nutritional interventions are efficacious in the prevention of falls and related injuries (e.g., fractures) among the elderly.

Chewing and swallowing difficulties are recognized risk factors for pressure ulcer development. Pressure ulcers are considered an avoidable medical error, preventable within reason by applying evidence-based practices (including nutritional care, as pressure ulcers are more likely when nutrition is inadequate). Pressure ulcers are reasonably preventable, in part, by assuring nutritional intakes are adequate. Furthermore, specific interventions including the use of specialized nutritional supplements help reduce the expected time to heal pressure ulcers once they have developed.

SUMMARY

As set forth in co-pending application U.S. Ser. No. 15/327,745, published as WO2016/012403 and herein incorporated by reference in its entirety, the inclusion of beta-glucan in a nutritional product surprisingly achieves a similar or identical (possibly even enhanced) effect of increasing the cohesiveness of the food bolus (e.g., for patients who have compromised secretion of saliva). However, the present inventors discovered that dosing beta-glucan as a rheology modifier to achieve a target extensional viscosity in nutritional formulations is very challenging (both for liquid or powder as a modifier) because the quantity needed to achieve significant extensional behavior is quite low (few wt. %). For this reason, the present inventors identified maltodextrin as a carrier ingredient that is either neutral toward or enhances the extensional properties of the final product. To the best knowledge of the inventors, no commercial solution providing high extensional viscosity to a composition in a controlled way for safe swallowing is available for patients.

Accordingly, in a general embodiment, the present disclosure provides a thickening powder formulated for dilution into at least a portion of a composition (e.g., a nutritional product and/or water), the thickening powder comprising beta-glucan and maltodextrin in an amount that is neutral toward or enhances extensional properties of the composition.

In an embodiment, the thickening powder further comprises a low molecular weight carbohydrate (e.g., sucrose and/or lactose).

In an embodiment, the maltodextrin is maltodextrin DE20.

In an embodiment, the thickening powder consists essentially of the beta-glucan and the maltodextrin. Preferably, the thickening powder consists of the beta-glucan and the maltodextrin.

In an embodiment, the thickening powder comprises the maltodextrin and the beta-glucan in a weight ratio of about 10:1 to about 300:1, preferably about 20:1 to about 200:1, more preferably about 20:1 to about 150:1 (e.g., about 150:1), most preferably about 20:1 to about 100:1.

In an embodiment, the thickening powder comprises the maltodextrin and an oat extract containing beta-glucan in a weight ratio of about 1:1 to about 30:1, preferably about 2:1 to about 20:1, more preferably about 2:1 to about 15:1 (e.g., about 15:1), most preferably about 2:1 to about 10:1, for example for an oat extract containing 14% beta-glucan. Preferably, the oat extract contains 10% to 18%, 12% to 16%, or more preferably 14% beta-glucan.

In an embodiment, the composition is a liquid composition.

In another embodiment, the present disclosure provides a method of making a thickening powder formulated for dilution into at least a portion of a composition (e.g., a nutritional product and/or water), the thickening powder comprising beta-glucan and maltodextrin in an amount that is neutral toward or enhances extensional properties of the composition. The method comprises: extracting the beta-glucan from a source selected from the group consisting of cereal, mushroom, yeast, seaweed, algae and mixtures thereof; and at least one step selected from the group consisting of (i) adding the maltodextrin to the source before the extracting of the beta-glucan from the source and (ii) adding the maltodextrin to the beta-glucan after the extracting of the beta-glucan from the source.

In an embodiment, the thickening powder further comprises a low molecular weight carbohydrate (e.g., sucrose and/or lactose).

In an embodiment, the thickening powder comprises the maltodextrin and the beta-glucan in a weight ratio of about 10:1 to about 300:1, preferably about 20:1 to about 200:1, more preferably about 20:1 to about 150:1 (e.g., about 150:1), most preferably about 20:1 to about 100:1.

In another embodiment, the thickening powder comprises the maltodextrin and an oat extract containing beta-glucan in a weight ratio of about 1:1 to about 30:1, preferably about 2:1 to about 20:1, more preferably about 2:1 to about 15:1 (e.g., about 15:1), most preferably about 2:1 to about 10:1, for example for an oat extract containing 14% beta-glucan.

In an embodiment, the source comprises oat bran.

In a preferred embodiment, the maltodextrin is added to the source before the extracting of the beta-glucan from the source.

In another embodiment, the present disclosure provides a method of making a composition (e.g., a nutritional product and/or a water-based beverage). The method comprises forming at least a portion of the composition by diluting a thickening powder comprising beta-glucan and maltodextrin in an amount that is neutral toward or enhances the extensional properties of the composition. The diluting of the thickening powder can comprise diluting the thickening powder in a liquid comprising at least one of water or milk, at a liquid:powder weight ratio of 100:1 to 15:1.

The thickening powder can further comprise a low molecular weight carbohydrate (e.g., sucrose and/or lactose). The thickening powder can consist essentially of the beta-glucan, the maltodextrin and the optional low molecular weight carbohydrate. Preferably, the thickening powder can consist of the beta-glucan, the maltodextrin and the optional low molecular weight carbohydrate. The thickening powder can comprise the maltodextrin and the beta-glucan in a weight ratio of about 10:1 to about 300:1, preferably about 20:1 to about 200:1, more preferably about 20:1 to about 150:1 (e.g., about 150:1), most preferably about 20:1 to about 100:1.

The aqueous solution can be present in the composition in an amount that provides to the composition a shear viscosity of about 1 mPas to about 200 mPas, preferably about 2 mPas to about 100 mPas, more preferably about 4 mPas to about 50 mPas, most preferably from about 5 mPas to about 20 mPas, all values measured at a shear rate of 50 s$^1$ and 20° C., and a relaxation time determined by a Capillary Breakup Extensional Rheometry (CaBER) experiment of about 10 to about 2,000 milliseconds (ms), preferably about 20 ms to about 1,000 ms, more preferably about 50 ms to about 500 ms, and most preferably from about 100 ms to about 200 ms, all values measured at a temperature of 20° C.

In another embodiment, the present disclosure provides a composition (e.g., a nutritional product and/or a water-based beverage) comprising: an aqueous solution comprising beta-glucan and maltodextrin in an amount that is neutral toward or enhances extensional properties of the composition. The composition comprises an amount of the aqueous solution that provides to the composition a shear viscosity of about 1 mPas to about 200 mPas, preferably about 2 mPas to about 100 mPas, more preferably about 4 mPas to about 50 mPas, most preferably from about 5 mPas to about 20 mPas, all values measured at a shear rate of 50 s$^1$ at 20° C., and a relaxation time determined by a Capillary Breakup Extensional Rheometry (CaBER) experiment of about 10 to about 2,000 milliseconds (ms), preferably about 20 ms to about 1,000 ms, more preferably about 50 ms to about 500 ms, and most preferably from about 100 ms to about 200 ms, all values measured at a temperature of 20° C. Preferably, the composition is a water-based beverage, more preferably, the composition is a liquid composition, even more preferably a thin liquid composition. The composition can be used for the treatment of dysphagia.

In another embodiment, the present disclosure provides a method of treating a swallowing disorder in an individual having the swallowing disorder. The method comprises orally administering to the individual a composition (e.g., a nutritional product and/or a water-based beverage) comprising an aqueous solution comprising beta-glucan and maltodextrin in an amount that is neutral toward or enhances extensional properties of the composition. The composition comprises an amount of the aqueous solution that provides to the composition a shear viscosity of about 1 mPas to about 200 mPas, preferably about 2 mPas to about 100 mPas, more preferably about 4 mPas to about 50 mPas, most preferably from about 5 mPas to about 20 mPas, all values measured at a shear rate of 50 s$^{-1}$ at 20° C., and a relaxation time determined by a Capillary Breakup Extensional Rheometry (CaBER) experiment of about 10 to about 2,000 milliseconds (ms), preferably about 20 ms to about 1,000 ms, more preferably about 50 ms to about 500 ms, and most preferably from about 100 ms to about 200 ms, all values measured at a temperature of 20° C.

In another embodiment, the present disclosure provides a method of promoting safe swallowing of a composition (e.g., a nutritional product and/or water) in an individual in need thereof. The method comprises: adding to the composition an aqueous solution comprising beta-glucan and maltodextrin in an amount that is neutral toward or enhances extensional properties of the composition. The aqueous solution is added to the composition in an amount that provides to the composition a shear viscosity of about 1 mPas to about 200 mPas, preferably about 2 mPas to about 100 mPas, more preferably about 4 mPas to about 50 mPas, most preferably from about 5 mPas to about 20 mPas, all values measured at a shear rate of 50 s$^{-1}$ at 20° C., and a relaxation time determined by a Capillary Breakup Extensional Rheometry (CaBER) experiment of about 10 to about 2,000 milliseconds (ms), preferably about 20 ms to about 1,000 ms, more preferably about 50 ms to about 500 ms, and most preferably from about 100 ms to about 200 ms, all values measured at a temperature of 20° C. The method comprises administering to the individual the composition to which the aqueous solution has been added.

In another embodiment, the present disclosure provides a method of mitigating a risk of aspiration during swallowing of a composition (e.g., a nutritional product and/or water) in an individual in need thereof. The method comprises: adding to the composition an aqueous solution comprising beta-glucan and maltodextrin in an amount that is neutral toward or enhances extensional properties of the composition. The aqueous solution is added to the composition in an amount that provides to the composition a shear viscosity of about 1 mPas to about 200 mPas, preferably about 2 mPas to about 100 mPas, more preferably about 4 mPas to about 50 mPas, most preferably from about 5 mPas to about 20 mPas, all values measured at a shear rate of 50 s$^{-1}$ at 20° C., and a relaxation time determined by a Capillary Breakup Extensional Rheometry (CaBER) experiment of about 10 to about 2,000 milliseconds (ms), preferably about 20 ms to about 1,000 ms, more preferably about 50 ms to about 500 ms, and most preferably from about 100 ms to about 200 ms, all values measured at a temperature of 20° C. The method comprises administering to the individual the composition to which the aqueous solution has been added. Preferably, the composition is water.

In another embodiment, the present disclosure provides a method for improving the cohesiveness of a composition (e.g., a nutritional product and/or water). The method comprises forming at least a portion of the composition by diluting a thickening powder comprising beta-glucan and maltodextrin in an amount that is neutral toward or enhances the extensional properties of the composition. The aqueous solution can be present in the composition in an amount that provides to the composition a shear viscosity of about 1 mPas to about 200 mPas, preferably about 2 mPas to about 100 mPas, more preferably about 4 mPas to about 50 mPas, most preferably from about 5 mPas to about 20 mPas, all values measured at a shear rate of 50 s$^1$ at 20° C., and a relaxation time determined by a Capillary Breakup Extensional Rheometry (CaBER) experiment of about 10 to about 2,000 milliseconds (ms), preferably about 20 ms to about 1,000 ms, more preferably about 50 ms to about 500 ms, and most preferably from about 100 ms to about 200 ms, all values measured at a temperature of 20° C.

An advantage of one or more embodiments provided by the present disclosure is to promote safer swallowing of boluses of a nutritional product in an individual suffering from dysphagia.

Another advantage of one or more embodiments provided by the present disclosure is to improve the lives of a large and growing number of individuals who suffer from dysphagia.

Yet another advantage of one or more embodiments provided by the present disclosure is to support specific interventions (e.g., to promote oral health, help restore normal swallowing, or reinforce a swallow-safe bolus) that can enable individuals to eat orally instead of being tube fed and/or requiring PEG placement and experience the psychosocial aspects of nutritional products associated with general well-being while guarding against the potentially negative consequences that result from lack of adequate swallowing ability.

Still another advantage of one or more embodiments provided by the present disclosure is to improve the intake of nutritional products by individuals who suffer from dysphagia and thus enable such individuals to swallow a wider variety of nutritional products safely and comfortably, which may lead to an overall healthier condition of the individual and prevent further health-related decline.

Furthermore, another advantage of one or more embodiments provided by the present disclosure is to provide natural cohesiveness that saliva typically provides to food boluses of nutritional products when being consumed by an individual.

Moreover, another advantage of one or more embodiments provided by the present disclosure is to modify rheological properties of a nutritional product to prevent bolus penetration and aspiration.

Another advantage of one or more embodiments provided by the present disclosure is a nutritional product having cohesiveness akin to saliva produced in the mouth and thus providing a more natural sensation to individuals who suffer from dysphagia.

Yet another advantage of one or more embodiments provided by the present disclosure is a nutritional product devoid of the thickened sensation (high shear viscosity) from conventional thickeners because one or more embodiments provided by the present disclosure leave no residue in the mouth of the individuals who suffer from dysphagia.

This is particularly relevant for liquid products that are supposed to maintain their thin liquid properties.

Still another advantage of one or more embodiments provided by the present disclosure is a nutritional product having organoleptic properties superior to known thickened nutritional products.

Furthermore, another advantage of one or more embodiments provided by the present disclosure is improved cohesion of food boluses to prevent a food bolus from being broken into smaller fragments which may enter the airway or leave unwanted residues in the oropharyngeal and/or esophageal tract during the swallowing process.

Moreover, another advantage of one or more embodiments provided by the present disclosure is reduction of swallowing effort for individuals who suffer from dysphagia.

Another advantage of one or more embodiments provided by the present disclosure is reduced risk of residue build-up in the oropharyngeal and/or esophageal tracts of a dysphagia patient.

Yet another advantage of one or more embodiments provided by the present disclosure is increased cohesiveness and improved nutritional intake for individuals who suffer from dysphagia by enabling the individuals to swallow a wider variety of food and beverage products safely and comfortably, e.g., by improving bolus integrity ("cohesiveness") and thus lending confidence to the individuals who suffer from dysphagia that the individual is able to consume a wider range of products.

Still another advantage of one or more embodiments provided by the present disclosure is improved ability and efficiency to swallow and thus improved safety through reduced risk of pulmonary aspiration.

Furthermore, another advantage of one or more embodiments provided by the present disclosure is greater independence from feeding assistance and/or reduced length of time spent in feeding-assistance during meal consumption.

Additional features and advantages are described herein and will be apparent from the following Figures and Detailed Description.

BRIEF DESCRIPTION OF THE FIGURES

FIG. 2 is a table showing the results from the experimental example disclosed herein.

DETAILED DESCRIPTION

Definitions

Figure 1:
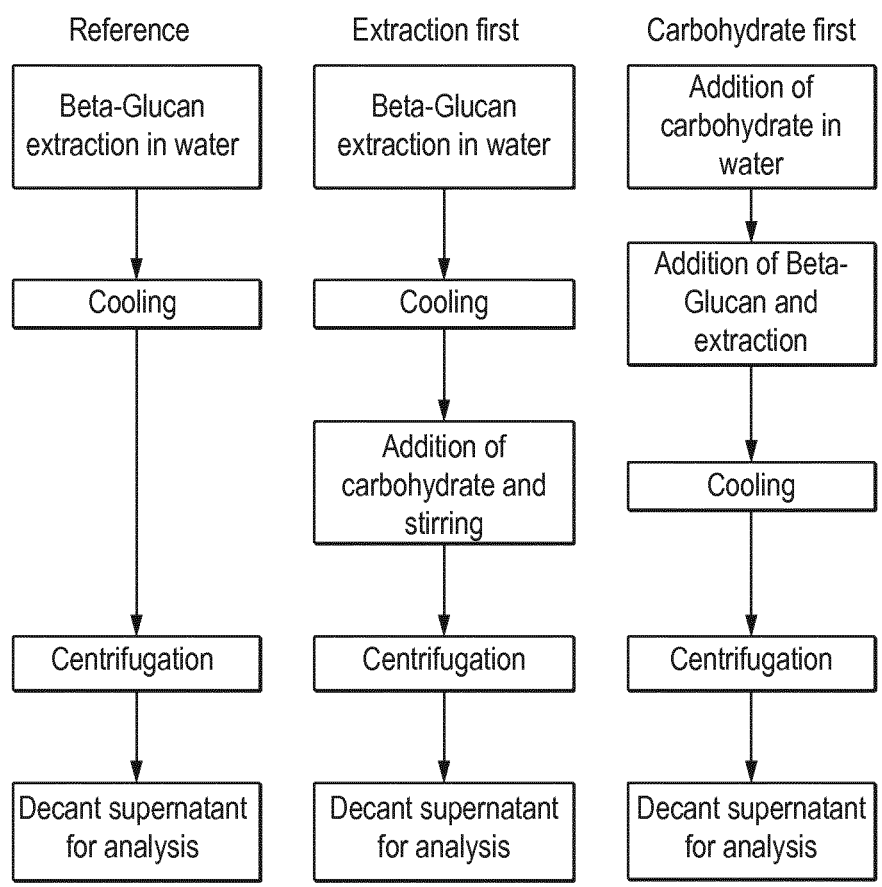
FIG. 1 is a flowchart showing the processes used in the experimental example disclosed herein.
Figure 3:
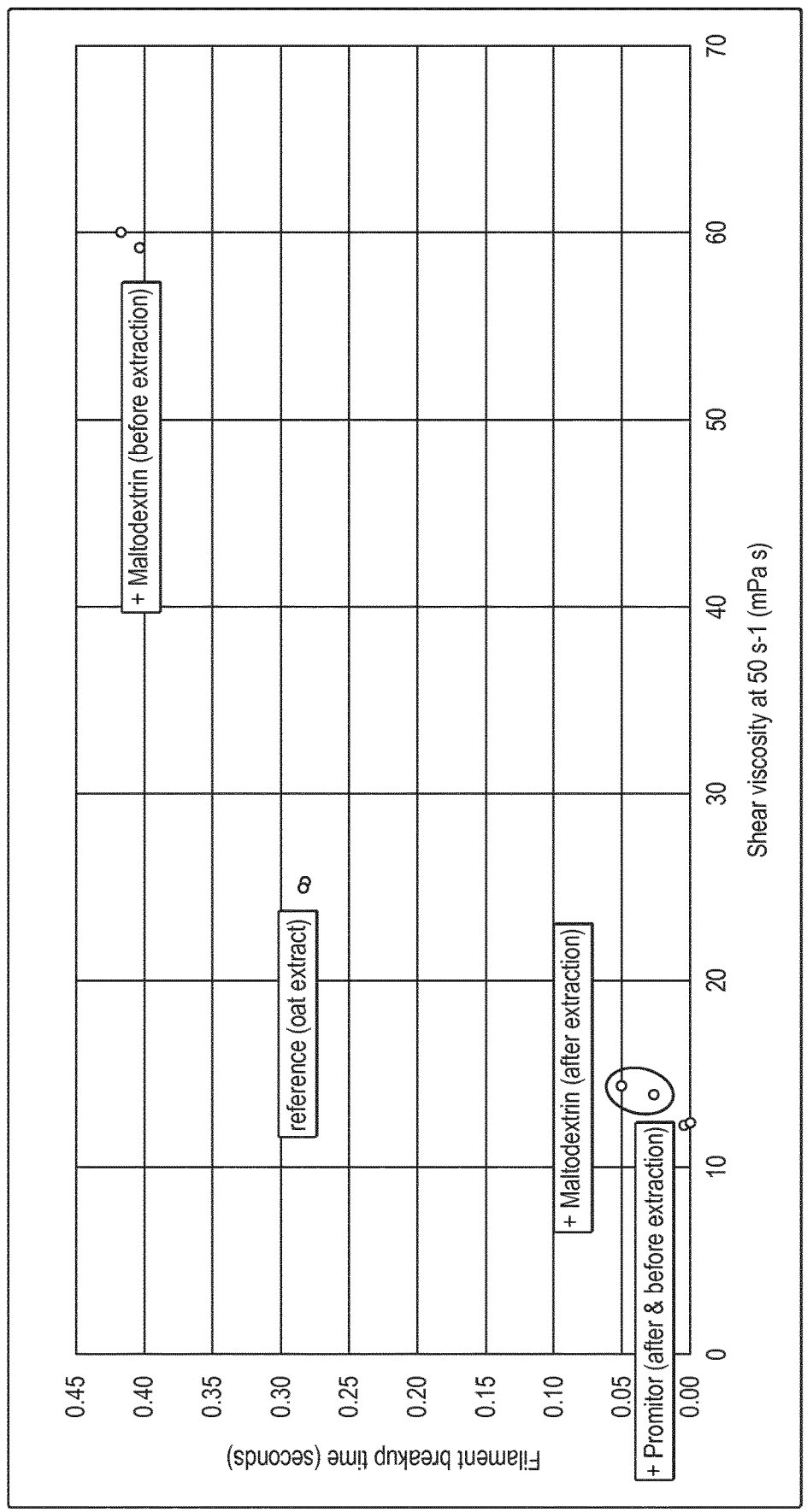
FIG. 3 is a graph showing the results from the experimental example disclosed herein.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. Weight by total solids as noted as "% TS."

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "an ingredient" or "the ingredient" includes two or more ingredients.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 75 wt. % of the referenced components, preferably at least 85 wt. % of the referenced components, more preferably at least 90 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

The term "nutritional product" means a product or composition that is intended for ingestion by an individual such as a human and provides at least one nutrient to the individual.

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. These terms also refer to the maintenance and/or promotion of health in an individual not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

The term "individual" means any animal, including humans, that could suffer from cognitive aging and thus benefit from one or more of the methods disclosed herein. Generally, the individual is a human or an avian, bovine, canine, equine, feline, hicrine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the individual is a human or a companion animal such as a dog or cat.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "promote," "improve," "increase," "enhance" and the like refer to the effects of a nutritional product comprising the thickening powder disclosed herein relative to a nutritional product lacking the thickening powder, but otherwise identical.

"Beta-glucan" and "β-glucan" refer to homopolysaccharides of D-glucopyranose monomers linked by (1→3), (1→4) glycosidic bonds. Beta-glucan is derivable from plant or microbial origin, e.g. from cereal (e.g., oats, barley), certain types of mushrooms (e.g., reishi, shiitake, maitake), yeasts, seaweed, and algae, by methods known to the skilled person, for example as described by Lazaridou et al. in "A comparative study on structure-function relations of mixed-linkage (1→3), (1→4) linear ⊖-D-glucans" in Food Hydrocolloids, 18 (2004), 837-855.

The term "maltodextrin" refers to polysaccharides that consist of D-glucose units connected in chains of variable length. The glucose units are primarily linked via α (1→4) glycosidic bonds. Maltodextrins are classified by DE (dextrose equivalent), and have a DE between 3 and 20.

Embodiments

In an aspect of the present disclosure, a thickening powder can be diluted in a liquid comprising at least one of milk or water to form at least a portion of a composition (e.g., a nutritional product or water-based beverage). The powder comprises beta-glucan and maltodextrin in an amount that is neutral toward or enhances the extensional properties of the composition. Optionally, the thickening powder can comprise the maltodextrin in combination with a low molecular weight carbohydrate (e.g., sucrose and/or lactose).

In an embodiment, the thickening powder comprises the maltodextrin and the beta-glucan in a weight ratio of about 10:1 to about 300:1, preferably about 20:1 to about 200:1, more preferably about 20:1 to about 150:1 (e.g., about 150:1), most preferably about 20:1 to about 100:1.

In an embodiment, the thickening powder comprises the maltodextrin and an oat extract containing beta-glucan in a weight ratio of about 1:1 to about 30:1, preferably about 2:1 to about 20:1, more preferably about 2:1 to about 15:1 (e.g., about 15:1), most preferably about 2:1 to about 10:1, for example for an oat extract containing 14% beta-glucan. Preferably, the oat extract contains 10% to 18%, 12% to 16%, or more preferably 14% beta-glucan.

Preferably the composition resulting from dilution of the powder is a beverage having a nectar consistency. More preferably, the composition resulting from dilution of the powder is a beverage having a water-like consistency.

To form the powder, a composition comprising the beta-glucan can be spray-dried, freeze-dried or subjected to any other procedure of drying known in the art. Additionally or alternatively, the powder can be made by dry mixing.

The powder can be provided to the consumer in a container (e.g., a sealed container) for reconstitution in the container and/or for allowing the user to pour the powder from the container into a drinking receptacle in which the powder is reconstituted. Non-limiting examples of suitable containers include bags, boxes, cartons, bottles, or combinations thereof. Preferred containers include a sachet/stick pack, i.e., a small disposable pouch, typically of flexible film such as cellophane or paper, preferably capable of being torn open at one or both ends, and containing one serving of the composition.

In an embodiment, the powder does not contain any protein. In an embodiment, the powder does not contain any fat or oil. In an embodiment, the powder does not contain any carbohydrate additional to the maltodextrin and the optional low molecular weight carbohydrate. For example, the powder can consist essentially of or consist of the beta-glucan, the maltodextrin, and the optional low molecular weight carbohydrate.

In another aspect, a method of treating a swallowing disorder in an individual having the swallowing disorder comprises administering to the individual a composition comprising a diluted powder comprising beta-glucan and maltodextrin in an amount that is neutral toward or enhances the extensional properties of the composition. In a further aspect, a method of mitigating the risk of aspiration during swallowing of a composition in an individual having dysphagia comprises administering to the individual the composition, and the composition comprises a diluted powder comprising beta-glucan and maltodextrin in an amount that is neutral toward or enhances the extensional properties of the composition.

Beta-glucan and hence also oat show particularly preferable properties in the powder because small amounts of beta-glucan can provide advantageous shear viscosities and relaxation times. Preferably, the shear viscosities are low and the relaxation times are long. The shear viscosity of a product is determined by any method that can accurately control the shear rate applied to the product and simultaneously determine the shear stress or vice versa. Standard methods include the use of concentric cylinders, cone-and-plate and plate-plate geometries. Relaxation times can be determined in this context by a Capillary Breakup Extensional Rheometry (CaBER) as known in the art. The shear viscosity of a product is measured at the same temperature as the relaxation time.

Shear viscosity is a measurable rheological property. Shear viscosity is often referenced as viscosity and describes the reaction of a material to applied shear stress. In other words, shear stress is the ratio between "stress" (force per unit area) exerted on the surface of a fluid, in the lateral or horizontal direction, to the change in velocity of the fluid as you move down in the fluid (a "velocity gradient"). The shear viscosity confers the thickened sensation to a product.

Another rheological property of a material is its extensional viscosity. Extensional viscosity is the ratio of the stress required to extend a liquid in its flow direction to the extension rate. Extensional viscosity coefficients are widely used for characterizing polymers, where they cannot be simply calculated or estimated from the shear viscosity. Rheological studies are generally performed using rheometers, which generally impose a specific stress field or deformation to the fluid and monitor the resultant deformation or stress. These instruments may operate in steady flow or oscillatory flow, as well as both shear and extension. The extensional viscosity may provide a product with an increased cohesiveness without the provision of a thickened sensation.

The composition is preferably orally administrable, for example as one or more of a pharmaceutical formulation, a nutritional product, a dietary supplement, a functional food or a beverage product.

In a further aspect, a method for improving the cohesiveness of a composition comprises adding a diluted powder comprising beta-glucan and maltodextrin in an amount that is a carbohydrate that is neutral toward or enhances the extensional properties of the composition to one or more ingredients of the composition. The composition can be a nutritional product, and the one or more ingredients of the nutritional product can be selected from the group consisting of a protein, an amino acid, a fat, a carbohydrate, a prebiotic, a probiotic, a fatty acid, a phytonutrient, an antioxidant, and/or combinations thereof.

The protein in the nutritional product can be one or more of a dairy-based protein, a plant-based protein or an animal-based protein. Non-limiting examples of suitable dairy-based protein include casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Non-limiting examples of suitable plant-based protein include, for example, soy protein (e.g., all forms including concentrate and isolate), pea protein (e.g., all forms including concentrate and isolate), canola protein (e.g., all forms including concentrate and isolate), other plant proteins such as wheat and fractionated wheat proteins, corn and it fractions including zein, rice, oat, potato, peanut, green pea powder, green bean powder, and any proteins derived from beans, lentils, and pulses. Non-limiting examples of suitable animal-based protein include beef, poultry, fish, lamb, seafood and combinations thereof.

Non-limiting examples of suitable fat for the nutritional product include vegetable fat (such as olive oil, corn oil, sunflower oil, rapeseed oil, hazelnut oil, soy oil, palm oil, coconut oil, canola oil, lecithins, and the like), animal fat (such as milk fat) or any combinations thereof.

Non-limiting examples of suitable carbohydrates for the nutritional product (additional to the maltodextrin) include glucose, fructose, corn syrup solids, modified starch, amylose starch, tapioca starch, corn starch or any combinations thereof. In an embodiment, the nutritional product can comprise soluble fiber and/or insoluble fiber. Non-limiting examples of suitable soluble fiber includes fructooligosaccharides, acacia gum, inulin, and mixtures thereof. A non-limiting example of suitable insoluble fiber includes pea outer fiber.

Example

The following non-limiting example is an experimental example supporting one or more embodiments of the thickening powder provided by the present disclosure. The processes used in the experiments are set forth in FIG. 1.

The aim of the experimental trial was to attempt to add up to 30% TS of soluble corn fiber (PROMITOR®) or up to 30% TS of maltodextrin DE20 to a 1.64% TS of oat bran (OATWELL®) containing 14% beta-glucan at different pHs. The resultant concentrations were about 0.23% beta-glucan and about 28.36% carrier ingredient.

In a first test, the carrier raw material was added to the beta-glucan after the extraction of the beta-glucan from oat bran. Specifically, the beta-glucan was extracted from the oat bran (OATWELL®) for thirty minutes at 60° C.; then the beta-glucan extract was cooled to 15° C.; one portion (reference) was directly centrifuged at 15° C. and 2939×g for 20 min, the insoluble material decanted and the supernatant separated and collected for analysis. A second portion and third portion of the extract were mixed with the soluble corn fiber or the maltodextrin DE20 in order to reach 30% TS; both samples were centrifuged at 15° C. and 2939×g for 20 min, the insoluble material decanted and the supernatant separated and collected for analysis. Three final sample were obtained, i.e., one beta-glucan extract, another beta-glucan extract with soluble corn fiber, and another beta-glucan extract with maltodextrin DE20. The pH of each variant was measured and one portion of each sample was adjusted with citric acid 5% to pH 6.0. Viscosity and cohesiveness of all samples were measured.

The pHs of the samples without adjustment were 7.12 for the reference sample, 6.92 for the Promitor sample, and 6.91 for the maltodextrin sample.

In a second test, each carrier raw material was added to the oat bran before the beta-glucan extraction. Specifically, the maltodextrin DE20 or the soluble corn fiber was separately dissolved to reach 28.36% TS and mixed for fifteen minutes at 60° C.; then 1.64% the oat bran was added to each carrier dispersion in order to reach a final concentration of 30% TS. The oat bran and the carrier were stirred for thirty minutes at 60° C. and then cooled to 15° C. The pH of each variant was measured and one portion of each sample was adjusted with citric acid 5% to pH 6.0 Viscosity and cohesiveness of all samples were measured.

The results are shown in the table in FIG. 1 and the graph in FIG. 2.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating a swallowing disorder in an individual having the swallowing disorder, the method comprising administering to the individual a composition comprising:
   beta-glucan; and
   maltodextrin,
   the composition having a shear viscosity of about 1 mPas to about 200 mPas when measured at a shear rate of 50 s$^{-1}$ and a relaxation time determined by a Capillary Breakup Extensional Rheometry (CaBER) experiment of about 10 to about 2,000 milliseconds (ms) at a temperature of 20° C.,
   wherein the composition comprises the maltodextrin and the beta-glucan in a weight ratio of about 10:1 to about 300:1.

2. The method of claim 1, wherein the composition is a liquid.

3. The method of claim 1, wherein the maltodextrin is maltodextrin DE 20.

4. The method of claim 1, wherein the composition further comprises at least one of a sucrose or lactose.

* * * * *